United States Patent [19]
Urs

[11] 4,336,084
[45] Jun. 22, 1982

[54] METHOD FOR MAKING PRIMER CONSTITUENTS

[75] Inventor: Venkataramaraj S. Urs, Godfrey, Ill.

[73] Assignee: Olin Corporation, Stamford, Conn.

[21] Appl. No.: 182,362

[22] Filed: Aug. 29, 1980

[51] Int. Cl.³ .............................................. C06B 41/02
[52] U.S. Cl. ........................................ 149/24; 149/45; 149/105; 149/108.6; 149/109.6
[58] Field of Search ............... 149/24, 45, 105, 108.6, 149/109.6

[56] References Cited
U.S. PATENT DOCUMENTS 3,894,068 7/1975 Taylor .................................. 149/24
4,029,530 6/1977 Kenney ................................ 149/24

Primary Examiner—Stephen J. Lechert, Jr.
Attorney, Agent, or Firm—Bruce E. Burdick; William W. Jones

[57] ABSTRACT

An improved method for producing known primer constituents lead styphnate and barium nitrate, in situ, plus water. The process is carried out by reacting effective amounts of trinitroresorcinol (TNR), with barium hydroxide, or barium carbonate, and lead nitrate in water.

12 Claims, No Drawings

METHOD FOR MAKING PRIMER CONSTITUENTS

This invention relates to a process for producing, in situ, the known primer constituents lead styphnate and barium nitrate plus water. More specifically, the process of this invention involves the reaction of trinitroresorcinol, with barium oxide, barium hydroxide, or barium carbonate, and lead nitrate in water, to produce the lead styphnate and barium nitrate, plus an additional amount of water.

Typical percussion primer mixtures for use in shot shell, rim fire and center fire ammunition contain effective amounts of lead styphanate which is a primary high explosive, sensitizers such as tetracene, boosters such as pentaerythritol tetranitrate (PETN), oxygen-donating compounds such as barium nitrate or lead nitrate, and fuels such as aluminum powder, antimony sulfide, and calcium silicide. This ingredients are blended together in water for safety purposes, and are wet primed into a shot shell or center-fire primer cup or a rim fire case rim. The primed charges are then dried and thus made ready for use. In the case of rim fire primers, a frictionator such as ground glass may be added to the mixture.

The primary high explosive, lead styphnate, which is used in the above-noted primer manufacturing process, is generally prepared in thirty five to seventy pound batches, and smaller portions of the bulk supply of the lead styphnate are transferred to the mixing and blending device with the other constituents to produce the primer mix. Since lead styphnate is a highly percussion sensitive material, particularly when dry, the handling and storing of large bulk quantities of thirty five to seventy pounds of this material requires substantial safety precautions.

The bulk supply of lead styphnate is typically produced by reacting trinitroresorcinol with an excess of sodium hydroxide or magnesium oxide and acetic acid to form sodium or magnesium styphnate. The sodium or magnesium styphnate solution is then heated to about 140° F. and a large excess of aqueous solution of lead nitrate is added to produce a lead styphnate precipitate. The lead styphnate is then filtered out of the solution and washed free of soluble salts. The filtrate, which contains excess lead nitrate and the sodium or magnesium salts, as well as the wash waters, are then disposed of as waste materials. It will be apparent from the above, that the separate preparation of lead styphnate is undesirable since it takes time, utilizes expensive reagents, produces a waste material containing many of the process reagents, and can create an environmental pollution problem concerning disposal of the waste materials. In addition to the above-noted process for producing lead styphnate, a number of other processes for the production of lead styphnate are reviewed and discussed in U.S. Pat. No. 3,983,149, to Joseph F. Kenney granted Sept. 28, 1976.

The foregoing clearly points out the disadvantages of wastefulness of both time and materials, the additional expense, the safety problems, and the potential pollution problems which are all attendant to the prior art processes for producing lead styphnate for use in priming compositions.

The above-noted U.S. Pat. No. 3,983,149 to Kenney, as previously observed, presents an extensive review of the prior art processes for forming lead styphnate, and their attendant disadvantages. This patent then offers as a solution to the prior art problems, a method of producing lead styphnate in situ in a Hobart mixer, which is the device commonly used in the trade in blending the priming composition constituents prior to the actual placement of the priming charges in the primer cups or cartridge case rims. The Kenney process involves the reaction of styphnic acid (trinitroresorcinol) with a lead compound, such as lead oxide, lead hydroxide, basic lead carbonate, or lead carbonate, the reaction taking place in water and resulting in the in situ formation of lead styphnate plus water, and, in some instances with certain reagents, carbon dioxide is also formed. After the lead styphnate has been formed, the remaining primer constituents are added to the Hobart mixer and blended to form the priming mix. It should be noted that some of the priming constituents, such as gum arabic, tetracene, blue dye, and some fuels such as calcium silicide can be incorporated with the styphnic acid before the lead compound is added, since these compounds will not enter into the ensuing reaction. On the other hand, it should also be noted that the oxygen donor, such as lead nitrate or barium nitrate should definitely not be added until after the lead styphnate has been formed. The Kenney method also requires that pure styphnic acid be used in the reaction, since the use of commercial styphnic acid results in an excessively sticky mixture which clings to the charging equipment and prematurely hardens so that the mixture cannot be stored overnight.

This invention is directed toward a method of making the primer constituents lead styphnate and barium nitrate in situ, such as in a Hobart mixer. The remaining priming constituents are then added to the lead styphnate and barium nitrate and the primer mix is blended and ready to use in priming cartridges. In the method of this invention there are no waste products, no need to make larger than necessary amounts of lead styphnate styphnate needed to complete a priming run, whereby considerable cost savings are realized along with reduced safety hazards. The process of this invention permits the use of conventional commercial grade trinitroresorcinol, although it also can be performed with the purified TNR, which is an absolute requirement in the Kenney process referred to above. By forming both the lead styphnate and the barium nitrate in situ in a single reaction, there is achieved an intimate admixture of these two ingredients which is not likely to be achieved by physically blending these two constituents. In the process of this invention, the lead styphnate and barium nitrate are formed in situ by reacting TNR with barium oxide, barium hydroxide or barium carbonate and lead nitrate in the presence of water. The end products of this reaction are lead styphnate, barium nitrate and water. When the reactants are combined in water, an exothermic reaction immediately ensues with the temperature in the mixture reaching between 130° F. to 190° F. in sixty to one hundred seconds, the actual temperature reached being dependent upon the ambient temperature. The exothermic condition causes the reaction to go to completion in the very short time span of one to two minutes. After reaching the temperature peak, the mix temperature is observed to drop to as low as 100° F. within the next two to three minutes. Breaking down the reaction stepwise, the TNR exothermically reacts with the barium hydroxide to form barium styphnate, which immediately then reacts with the lead nitrate to form lead styphnate, and barium nitrate. Two molecules of water are formed for each molecule of lead styphnate and barium nitrate, one molecule of water being free and the other being loosely bonded to the lead styphnate, thus forming lead styphnate monohydrate.

The diagramed reaction is as follows:

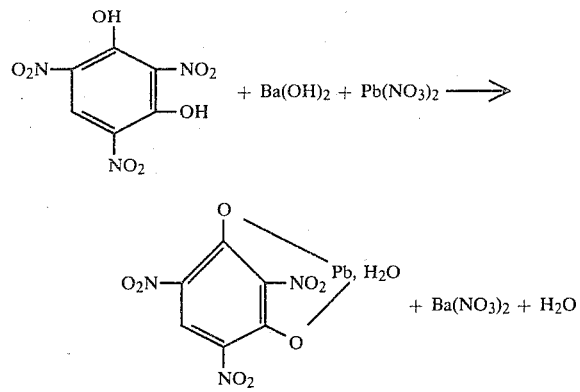

The reaction is, in general terms, carried out in the Hobart mixer as follows. Weighed amounts of TNR, barium hydroxide, and lead nitrate are put into the Hobart mixer in relatively dry form and a small amount of water, preferably five to ten percent by weight of the dry solids, is added to the mixer. The mixer is activated to stir the mixture during the reaction. After five minutes the mixer is stopped and the mixing paddle is cleaned to return mix adhering thereto to the remaining mixture. The mixing is then resumed for another ten minutes to assure completeness of the chemical reactions. After the subsequent mixing period of ten minutes, the adhering mix is knocked down into the mixer, the mix by this time being at ambient temperatures, and weighed quantities of remaining priming constituents, such as tetracene, PETN, antimony sulfide, aluminum, and a small amount of barium nitrate are added to the mix. A five percent solution of polyvinyl alcohol is added to the mixer to bring the moisture content of the mix suitable for working into primer cups. The entire mix is then blended for ten minutes to achieve admixture of all of the constituents, after which the priming mixture may be worked into primer cups in a conventional manner. The primer cups are foiled and dried, whereafter they are ready to be inserted into cartridges.

Specific examples of methods of forming priming mixes in accordance with this invention are as follows.

EXAMPLE 1

A three liter Hobart mixer was charged with 441 grams of lead nitrate, 252 grams of barium hydroxide monohydrate, 225 grams of antimony sulfide, and 102 grams of barium nitrate. These ingredients all were charged in a dry state and had been screened through a 30 mesh sieve. These ingredients were then mixed for five minutes in the Hobart mixer. The equivalent of 327 grams dry weight of wet TNR (making allowance for the moisture content) was added to the ingredients in the Hobart mixer along with 20 grams of water. Blending was then commenced and the exothermic reactor temperature rise was immediately apparent. Blending in the mixer was continued for five minutes after which the blending was stopped and the adherant mix was cleaned off of the mixing blade. Blending was then resumed and continued for ten minutes. The resultant mix was then analysed and showed to contain lead styphnate, barium nitrate, antimony sulfide, and water.

The pH of the mix was between 2 and 5, the acidity thereof demonstrating complete reaction of the barium hydroxide. Twenty five milliliters of five percent polyvinyl alcohol solution in water was then added to the mix, followed by 60 grams (dry weight) of tetrecene (using wet material, but making allowance for the water content), 75 grams of PETN and 90 grams of aluminum powder. Mixing was then continued for ten minutes to obtain a uniformly blended mix. The moisture content of the final mix was about fifteen percent. Chemical analysis of the mix showed the following percentages of the various components on a dry basis:

| Lead Styphnate | 39.8 |
| Tetracene | 3.7 |
| Barium Nitrate | 31.7 |
| Antimony Sulfide | 14.3 |
| PETN | 4.8 |
| Aluminum | 5.7 |

Shot shell primer cups were primed with the primer mix in the conventional wet priming procedure. The assembled primers exhibited good sensitivity, with three hundred of a total of three hundred all firing when a 2 ounce steel ball was dropped from a height of 6.8 inches on each primer mounted in a steel die. Five hundred of these primers were then assembled in 12 gage, 2¾ inch plastic shotshell tubes, using WC 490 Winchester nitrocellulose smokeless powder, 31.2 grains by weight, a cup and molded fiber wad, a low density polyethylene liner, 1¼ ounce lead shot, #4 chilled, with a six segment pie crimp closure. These five hundred shotshells were fired in five different shotguns at temperatures of 125° F., 170° F., 0° F., and −40° F. No misfires, hangfires or squibs were experienced in this test, and all of the rounds fired satisfactorily.

EXAMPLE 2

A three liter Hobart mixer was charged with 441 grams of lead nitrate, 252 grams of barium hydroxide monohydrate, 147 grams of barium nitrate, and 240 grams of antimony sulfide, these ingredients having been charged in the dry state after having been screened through a 30 mesh sieve. To the above mixture was added 327 grams dry weight of TNR, using wet TNR but making allowance for its water content, and 20 grams of water. The mixture was then blended in the Hobart mixer for five minutes, after which the mixer blade was cleaned, and blending then continued for an additional ten minutes. Then 25 milliliters of a 5 percent polyvinyl alcohol solution was added, along with 75 grams, dry weight, of tetracene, using wet material but making allowance for its water content, and 90 grams of PETN. Mixing then continued for an additional ten minutes. The mix was then examined for grittiness and uniformity. If the mix is found to be gritty and non-uniform, mixing can continue for an additional five to ten minutes. The moisture content of the blended mix was about fifteen percent. This mix was then charged into center fire pistol primer cups by the conventional wet priming process, foiled, fitted with anvils, and dried. Sensitivity tests performed on these assembled primer cups when assembled in caliber, 38 Special cartridge cases demonstrated satisfactory sensitivity characteristics.

EXAMPLE 3

A rim fire priming mix was formed by charging a Hobart mixer with 509.2 grams of lead nitrate, 293.7 grams of barium hydroxide monohydrate, these ingredients having been prescreened as outlined in the previous examples. To these ingredients there was added 376.9 grams of TNR, dry weight using wet TNR but making allowance for its water content, and 20 grams of water. These ingredients were blended in the Hobart mixer for a total of 15 minutes using the two step blending procedure described in the previous examples, and then 25 milliliters of a 5% polyvinyl alcohol solution, 105 grams of lead peroxide, and 330 grams of glass powder were added to the Hobart mixer. The contents of the Hobart mixer were then blended until a uniform texture mix was achieved.

Using a perforated metal charge leaf, .25 to .32 grain pellets of the priming mix were dropped into .22 caliber rim fire cartridge cases and the primer pellets were spun into the rims of the cases. The in-place primers were then dried and tested by the drop ball sensitivity procedure. The sensitivity was found to be uniformly acceptable indicating that the primed cases were suitable for loading into .22 caliber rim fire ammunition.

The above-outlined examples indicate the operability of primer compositions and the lead styphnate and barium nitrate constituents thereof formed in accordance with this invention for priming shotshell, center fire, and rim fire ammunition.

I should be noted that the chemical reactions performed in the examples outlined above, for every molecule of lead styphnate formed, one molecule of barium nitrate and two molecules of water are also formed. Examination of the lead styphnate crystals formed in the reaction shows them to be hexagonal, and apparently lead styphnate monohydrate molecules. Therefore, each time a lead styphnate monohydrate molecule is formed, there is a free molecule of water also formed. This results in a free moisture content of 3.8% and a total water content of 8% when dry initial reactants are used. Thus, the reaction forms water, which in turn, contributes to desensitization of the lead styphnate formed, during the preparation of the priming mix.

The initial reactants required for use in the method of this invention are trinitroresorcinol (also referred to as styphnic acid) and lead nitrate. The reactant which ultimately forms the primer oxydizer can be an oxygen-bearing compound such as barium hydroxide, barium hydroxide monohydrate, barium hydroxide octohydrate, barium oxide, barium carbonate, lead hydroxide, lead oxide, and lead carbonate. The barium compounds are preferred, and the barium hydroxide monohydrate is most preferred due to the attendant water molecule contained therein and its moderating influence on heat generation during its reaction with TNR. The resultant priming oxydizer obtained with the respective initial compounds listed above will be barium nitrate or lead nitrate. Mixtures of these initial compounds may be used to produce a suitable mixture of oxydizers in the priming mix.

It will be readily appreciated that this invention results in the formation of lead styphnate and a suitable oxydizer, in situ, in an intimate admixture, with lower costs, no waste by-products, and therefore, no pollution problems relating to disposal of waste by-products. This invention also provides for increased safety and reduced hazard since the primary explosive need not be produced, stored or handled in large bulk amounts, and need only be produced in batch amounts which will be utilized in a subsequent priming operation. While the preferred end products of the invention are lead styphnate and barium nitrate plus water, other oxygen donors such as lead nitrate can be produced in situ by practice of this invention, along with the lead styphnate. It should be noted that electrically fired primer mixes may also be formed using the process of this invention simply by adding to the priming mix a conductor, such as carbon.

Since many changes and variations of the disclosed embodiments of the invention may be made without departing from the inventive concept, it is not intended to limit the invention otherwise than as required by the appended claims.

I claim:

1. A method of forming a lead styphnate compound plus an oxygen-donating compound, in situ, for use in a priming mix, said method comprising reacting trinitroresorcinol with an oxygen-bearing compound selected from the group consisting of barium oxide, barium hydroxide compounds, barium carbonate, or mixtures thereof, in the presence of lead nitrate.

2. The mixture of lead styphnate compound and oxygen-donating compound produced by the method of claim 1.

3. A method of forming a lead styphnate compound plus an oxygen-donating compound, in situ, for use in a priming mix, said method comprising reacting trinitroresorcinol with an oxide, hydroxide or carbonate of a metal selected from the group consisting of barium in the presence of lead nitrate.

4. The mixture of lead styphnate and oxygen donating compound produced by the method of claim 3.

5. A method of forming a lead styphnate compound plus an oxygen-donating compound, in situ, for use in a priming mix, said method comprising reacting trinitroresorcinol with an oxygen bearing compound selected from the group consisting of barium oxide, barium hydroxide compounds, barium carbonate, or mixtures thereof, in the presence of lead nitrate and water.

6. A method of forming a lead styphnate compound plus an oxygen-donating compound, in situ, for use in a priming mix, said method comprising reacting trinitroresorcinol with an oxide, hydroxide, or carbonate of a metal selected from the group consisting of barium in the presence of lead nitrate and water.

7. A method of forming an intimate admixture of a lead styphnate compound and barium nitrate in situ, for use in a priming mix, said method comprising reacting trinitroresorcinol with a barium hydroxide compound in the presence of lead nitrate and water.

8. The method of claim 7, wherein said barium hydroxide compound is barium hydroxide monohydrate.

9. A method of forming an intimate admixture of a lead styphnate compound and barium nitrate, in situ, for use in a priming mix, said method comprising reacting trinitroresorcinol with a barium compound selected from the group consisting of barium oxide, barium hydroxide compounds and barium carbonate in the presence of lead nitrate and water.

10. A method of forming a priming mix comprising the steps of:

(a) reacting trinitroresorcinol with an oxygen bearing compound selected from the group consisting of barium oxide, barium hydroxide compounds, barium carbonate and mixtures thereof, in the presence of lead nitrate and water to form, in situ, a mixture of a lead styphnate compound and an oxygen donating compound;
(b) adding to said mixture effective amounts of a sensitizer, a booster, and a fuel; and
(c) mechanically blending the resulting mixture to form a relatively homogeneous mix of ingredients.

11. A method of forming a priming mix comprising the steps of:
(a) reacting trinitroresorcinol with a barium hydroxide compound in the presence of lead nitrate and water to form, in situ, a mixture of a lead styphnate compound and barium nitrate;
(b) adding to said mixture effective amounts of a sensitizer, a booster, and a fuel; and
(c) mechanically blending the resulting mixture to form a relatively homogeneous mix of ingredients.

12. The method of claim 11, wherein said barium hydroxide compound is barium hydroxide monohydrate.

* * * * *